United States Patent
Geinitz et al.

(10) Patent No.: US 11,137,365 B2
(45) Date of Patent: Oct. 5, 2021

(54) ASSEMBLY AND METHOD FOR MEASURING ELECTRICAL AND DIELECTRIC PROPERTIES OF A MATERIAL

(71) Applicant: Fraunhofer-Gesellschaft zur Foerderung der angewandten Forschung e. V., Munich (DE)

(72) Inventors: Steffen Geinitz, Augsburg (DE); Maximilian Eberhardt, Augsburg (DE)

(73) Assignee: FRAUNHOFER-GESELLSCHAFT ZUR FOERDERUNG DER ANGEWANDTEN FORSCHUNG E. V., Munich (DE)

( * ) Notice: Subject to any disclaimer, the term of this patent is extended or adjusted under 35 U.S.C. 154(b) by 142 days.

(21) Appl. No.: 16/654,744

(22) Filed: Oct. 16, 2019

(65) Prior Publication Data
US 2020/0340938 A1    Oct. 29, 2020

(30) Foreign Application Priority Data
Apr. 23, 2019 (DE) ............ 20 2019 102 278

(51) Int. Cl.
*G01R 31/00* (2006.01)
*G01N 27/22* (2006.01)

(52) U.S. Cl.
CPC ......... *G01N 27/221* (2013.01); *G01N 27/228* (2013.01)

(58) Field of Classification Search
USPC .................... 324/71.1, 674, 76.11
See application file for complete search history.

(56) References Cited

U.S. PATENT DOCUMENTS 6,496,018 B1 * 12/2002 Nagata ............... G01N 22/00
324/632
2016/0313269 A1   10/2016   Matvejev et al.
2018/0284045 A1   10/2018   Jahn et al.

FOREIGN PATENT DOCUMENTS

DE   20 2011 101 482 U1   9/2012
WO   2015/040037 A1       3/2015
WO   2017/060263 A1       4/2017

* cited by examiner

*Primary Examiner* — Vincent Q Nguyen
(74) *Attorney, Agent, or Firm* — Fitch, Even, Tabin & Flannery LLP

(57) ABSTRACT

The invention relates to an assembly and a method for measuring electrical and dielectric properties of a material having dielectric properties which vary over time, with a sensor that generates an electrical field interacting with the material and which is connected indirectly or directly to a signal generator. The signal generator generates an excitation signal that can be applied to the sensor which is able to generate a sensor signal depending on the electrical and dielectric properties of the material. An analog-digital converter converts the excitation signal and the sensor signal or analog signals derived therefrom into a digital excitation signal and digital sensor signal which can be supplied to a processor-based evaluation unit. The signal generator generates a multifrequency signal with a predetermined bandwidth as the excitation signal.

17 Claims, 4 Drawing Sheets

ASSEMBLY AND METHOD FOR MEASURING ELECTRICAL AND DIELECTRIC PROPERTIES OF A MATERIAL

CROSS REFERENCE TO RELATED APPLICATION

Reference is made to German Application No. 10 2019 102 278 filed Apr. 23, 2019, which is incorporated herein by reference in its entirety.

BACKGROUND OF THE INVENTION

Field of the Invention

The invention relates to an assembly and a method for measuring electrical and dielectric properties of a material having dielectric properties which vary over time, with a sensor that generates an electrical field, which is in or can be brought into operative connection with the material, which is connected indirectly or directly to a signal generator that generates an excitation signal that can be applied to the sensor and is able to generate a sensor signal depending on the electrical and dielectric properties of the material, and with an analog-digital converter for converting the excitation and the sensor signal or analog signals derived therefrom into a digital excitation signal and digital sensor signal which can be supplied to a processor-based evaluation unit.

Description of the Prior Art

Species-related assemblies and methods for carrying out dielectric analysis (DEA) are designed particularly for assessing the curing state of thermosets, paints, adhesives, composite materials and other types of polymers or organic substances by measuring the changes in their dielectric properties.

One great advantage of dielectric analysis is that it can be used under real processing or application conditions. Further an on-line evaluation is feasible which allows real time process control. Because of the large selection of different sensors, almost any practical application can be analysed such as spray coating, spreading with a doctor blade, application of materials with low or moderate viscosity, positioning of the sensor between the layers of a prepreg, immersion of the sensor in a liquid, mixture analysis and solvent evaporation.

The functional principle of dielectric analysis is similar to that of an impedance spectroscopy. In a typical measurement, a material sample is brought into direct contact with two electrodes of a dielectric sensor. The application of—for example—a sinusoidal excitation voltage forces charge carrier movements within the material sample: Positively charged particles migrate towards the negative terminal or align themselves with it, and vice versa. This movement gives rise to a sinusoidal current flow as a response signal with phase shift. In the frequency range up to about 1 MHz, the charge carriers are mainly ions, which often occur in the form of catalysts or impurities. But dipoles are also aligned in the electrical field. The amplitude and phase shift of the response signal depends on the mobility of the ions and dipoles. Because of this, dielectric analysis is the ideal method for examining crosslinking behaviour. As the curing reaction progresses, the sample material becomes more and more viscous. The mobility of the charge carrier is diminished, causing the amplitude in the resulting signal to decrease and the phase shift to increase.

The measured amplitude is linked to the dielectric permittivity $\varepsilon'$ and reflects the number of bipolar groups in the material sample. The dielectric loss factor $\varepsilon''$ is calculated from the phase shift and is a measure of the total energy dissipated by the arrangement of the dipoles and the ion movement inside the material. The value $\varepsilon''$ is also proportional to the ion conductivity $\sigma$, the reciprocal of the ionic viscosity v. The ionic viscosity v is a significant parameter for analysing crosslinking behaviour, characterizes the curing processes very well, and correlates with the dynamic viscosity.

Most of the sensors that are in contact with the material sample to be analysed consist of two interlocking comb electrodes which are mounted on a substrate. Because of the electrical field that penetrates the material sample, the sensors are suitable for carrying out local measurement of the dielectric properties of material sample areas and layers which are in direct contact with the sensor. The penetration depth of the electric field lines is approximately equal to the electrode gap.

One possible way to carry out these measurements is by generating and applying a "frequency sweep" over a predetermined spectral bandwidth at the measuring sensor. In this process, certain frequencies are set and measured sequentially, that is to say one after the other in time. The most frequently used test signal is a simple sinusoidal signal because with this signal the best signal results, in terms of the signal-to-noise ratio (SNR), can be obtained. See for example B. Sanchez, G. Vandersteen, R. Bragos, and J. Schoukens, "Basics of Broadband Impedance Spectroscopy Measurements Using Periodic Excitations," Measurement Science and Technology, vol. 23, no. 10, p. 105501, 2012, http://stacks.iop.org/0957-0233/23/i=10/a=105501. The disadvantage of such a measuring principle is that at least one complete period of the input and output signal must be measured in order to be able to carry out a signal analysis. This limits the real-time capability of the measurement, because it is not possible to record multiple data points simultaneously. Alternative known test signals are binary or impulse/chirp signals. The analysis of the signals can be performed using various measurement principles.

The simplest, but also the most error-prone measurement method for determining the response signal uses a shunt resistor. See also J. D. Menczel and R. B. Prime, Thermal Analysis of Polymers: Fundamentals and Applications, John Wiley, 2009. A more complex measuring setup which is described in the preceding article uses an "impedance measurement bridge". In this method, a controller is used to control and measure the voltage with a variable test impedance. The corresponding parameters can then be derived from this control data afterwards. Finally, the use of a transimpedance amplifier (TIA) is known in this context, which converts an input current into a proportional output voltage. The conversion ratio is controlled by a feedback network, consisting of resistors and/or capacitors.

Patent WO 2015/040037 A1 describes a sensor for a dielectric examination of a biological sample.

Patent DE 20 2011 101 482 U1 discloses an apparatus for capturing material properties of a medium, having a measuring device including a sensor device which is connected to the medium, and an actuation device for actuating the sensor device with signals in a predetermined frequency range, and a control device for controlling the operation of the measuring device and ordering the predetermined frequency ranges, wherein the actuation device is designed to determine the progression of the impedance Z of the medium according to the predetermined frequency range depending on the frequency and to output a detection signal. The control device is designed to evaluate the detection signal of the actuation device, determine a plurality of characteristic points on the impedance progression and to generate a results signal regarding the properties of the medium.

Patent WO 2017/060263 A1 discloses a dielectric measurement sensor for a measurement system suitable for dielectric impedance spectroscopy, wherein the measurement sensor at least in one operating state of the measurement sensor comprises at least one first microstrip line consisting of a first conductor strip for a measurement signal, a first dielectric substrate and a first ground surface, wherein the first conductor strip may be applied from the outside and over an area to a container containing a dielectric material sample to be measured which preferably is a pipe, a vessel or a bag.

SUMMARY OF THE INVENTION

The object invention is an assembly and a method for measuring electrical and dielectric properties of a material having dielectric properties which vary over time, with a sensor that generates an electrical field, which is in or can be brought into operative connection with the material, which is connected indirectly or directly to a signal generator which generates an excitation signal that can be applied to the sensor and is able to generate a sensor signal depending on the electrical and dielectric properties of the material, and with an analog-digital converter for converting the excitation and the sensor signal or analog signals derived therefrom into a digital excitation signal and digital sensor signal which can be supplied to a processor-based evaluation unit in such manner as to enable a real time measurement with improved signal quality and reduced effort for purposes of signal evaluation. Thus, it should be possible to carry out material examinations with shorter measuring periods. In addition, a further objective is to obtain the most comprehensive information possible on materials whose physical material properties change within extremely short time spans, i.e. within fractions of a second.

For the purposes of the invention, the assembly and method for measuring electrical and dielectric properties of a material having dielectric properties that change over time is characterized in that the signal generator generates a multifrequency signal with a predetermined bandwidth as the excitation signal.

The multifrequency signal, which may be generated by means of the signal generator, comprises within the predetermined bandwidth at least two simultaneous excitation modes, each with different excitation frequencies and different excitation signal amplitudes, each of which generate electrical alternating fields that interact with the sample at the same time at the respective excitation frequencies. The sensor signal, which depends on the electrical and dielectric properties of the material, comprises spectrally spread and simultaneous response signal components resulting from each of the excitation modes of the multifrequency signal, which are evaluated preferably under real time conditions in a subsequent signal processing operation. For this purpose, a processor-based evaluation unit, which is preferably a digital evaluation unit in the form of a FPGA and/or microcontroller, for example, captures and processes all spectral response signal components contained in the sensor and response signal at least within the limits of the predetermined bandwidth simultaneously on the basis of the digitalized sensor and excitation signal. The signal evaluation is preferably performed in situ, that is, while the measurement is being taken, but it may also be carried out with a time offset relative to the measurement.

The evaluated sensor signal may be displayed for further analysis or review on a display unit, in the form of a monitor for example, by representing all frequency- and time-dependent response signal components.

As a preferred excitation signal, the signal generator generates a modulated multi-sine. Basically, the multi-sine consists of multiple sine tones of different frequencies superimposed on each other, which in the present case are modified at least by an amplitude modulation, so that the amplitudes of the individual excitation modes differ from each other. Optionally, the multi-sine is also phase-modulated to avoid undesirable amplitude crosstalk.

The excitation is predominately performed with a multi-sine signal, but is not limited to this special kind of frequency modulated signal. The setup basically works for every time synchronously modulated signal as long as the time-wise order of the appearance of the signal components does not matter. As long as the signal can be applied simultaneously, any analog signal can be converted by the circuit and analyzed by the according algorithms.

The amplitude modulations and/or the choice of the excitation frequencies of the individual excitation modes within the specified bandwidth of the de-excitation signal are preferably subject to a rule or distribution pattern which may be chosen variously depending on the measurement task. For example, the following distribution patterns may be used:

The excitation frequencies of the individual excitation modes each have an equidistant frequency spacing between respective spectrally adjacent excitation modes or are subject to a statistical distribution. A distribution of the excitation frequencies dictated by algebraic or transcendent mathematical function, for example a logarithmic or exponential signal, is also possible. The preceding distribution patterns may also be applied for the selection of the amplitudes of the individual excitation modes. The choice of both the frequency and the amplitude for the individual excitation modes may preferably be made with consideration for the specific material properties of the material that is to be analysed, as for example using empirically acquired observations.

The excitation signal has a predetermined bandwidth preferably from 100 Hz to 100 MHz, particularly preferably from 100 Hz to 10 MHz or from 100 Hz to 1 MHz The amplitude spectrum of the individual excitation modes within the bandwidth is preferably also adjusted according to the characteristics of the measurement system in order to ensure that the energy is distributed as evenly as possible or chosen according to the user's wishes within the predetermined bandwidth.

The quality of the results of measurement can be influenced decisively by a choice of excitation signal which is adapted with the aid of the signal generator to the individual particularities of the measurement to be carried out.

The sensor signal in the form of a sensor current which is generated using the sensor is applied to a transimpedance amplifier (TIA) which performs a current voltage conversion for the purpose of the subsequent sensor signal processing. The very small sensor currents, which can be as low as in the pA range, can be amplified by the TIA by factors preferably in the higher dB range, preferably 20-100 dB, and so transferred to ranges in which signal processing can be carried out more effectively.

Alternatively or in combination, the sensor signal can be applied to a transimpedance amplifier circuit, which extends the bandwidth, ensures stability of the TIA and enhances S/N.

The TIA connected to the sensor is followed by at least one or one further amplification stage, preferably in the form of an operation amplifier circuit, which further amplifies and filters the sensor signal that has preferably been pre-amplified by the TIA to obtain an amplified and also filtered sensor signal. The at least one further filtering amplifier stage, of which the signal amplification factor is preferably in the 3-10 dB range, serves mainly to improve the signal for further, faultless analysis. An increase in the sensor signal amplitude brought about by the amplifier is advantageous because the minimum signal levels of the sensor signals are susceptible to interference from nearby electronic devices and of the network lines are very large and should be minimized.

After the analog, voltage-converted sensor signal has been amplified and filtered, it is converted into a digital sensor signal by an analog-digital converter, to which the analog excitation signal is also fed to be converted into a digital excitation signal. The digital excitation and sensor signals are passed to a processor-based evaluation unit, in which a Fourier transformation-based algorithm performs a Fourier transformation on the digital excitation and sensor signals. The processor-based evaluation unit further contains one algorithm for calculating a frequency-dependent impedance (Z) that can be assigned to the material and a frequency-dependent phase angle (θ) between the excitation and sensor signals based on the digital excitation and sensor signals. The processor-based evaluation unit further operates using at least one algorithm with which at least one of the following material properties of the material can be calculated on the basis of the frequency-dependent impedance (Z) and/or the frequency-dependent phase angle (θ): ion conductivity, ion viscosity, relative permittivity, imaginary permittivity, absolute permittivity, loss factor, specific resistance and capacitance, total resistance and capacitance.

Alternative to using FFT analysis, the processor-based evaluation unit evaluates the digital excitation and sensor signals based on a wavelet, based on characteristics of the material. The excitation signal is the same multi-sine with known frequency components. But instead of FFT algorithm, a wavelet transform is performed on the data to find out about changes in the signal over time. The information density to be extracted from the sample can be maximized by a repeated application of several wavelet analyses.

As part of the signal and data evaluation inside the processor-based evaluation unit, frequency-dependent characteristic values are created for all spectrally contained signal information included in the digital sensor signal. The characteristic values are accordingly calculated for each excitation frequency. The material properties described previously represent possible characteristic values.

In order to be able to evaluate material-variable processes, the characteristic values are recorded over the course of time. That is the material to be examined is exposed to a multiplicity of sensor-generated excitation signals in a short space of time. The further evaluation of the numerically obtained characteristic values may be carried out graphically on a monitor or based on the characteristic values themselves.

An example of a graphical evaluation is presented and explained in greater detail with reference to the following figures.

The assembly according to the invention allows not only the detection and analysis of dynamically variable material parameters in substances or substance mixtures, preferably exhibiting viscosity changes but also the detection and analysis of changes in the material composition and also of moisture within the materials based on the change in permittivity associated therewith.

BRIEF DESCRIPTION OF THE DRAWINGS

The invention will be described in exemplary terms without limitation of the general inventive thought, based on embodiments thereof and with reference to the drawing. In the drawing.

DETAILED DESCRIPTION OF THE INVENTION

Figure 1:
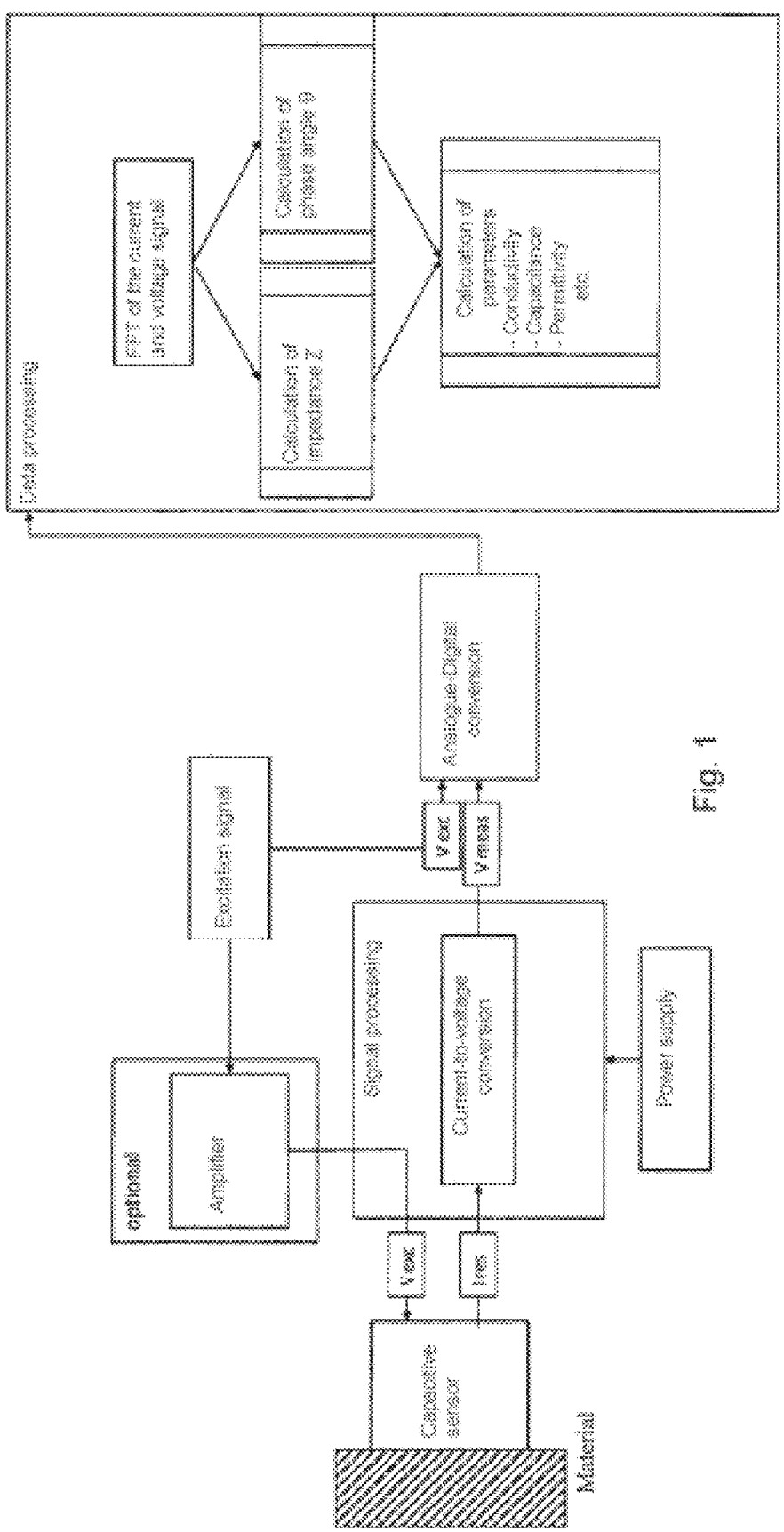
FIG. 1 shows an overview with components relating to the measurement and evaluation unit.

FIG. 1 is a schematic representation of the structure of an assembly for measuring electrical and dielectric properties of a material, which is shaded, which has a reciprocating connection with a capacitive sensor. The excitation signal required is generated by a function generator and if necessary pre-amplified with a fixed amplification factor by an amplifier to achieve a correspondingly strong reaction in the material sample (shaded). The excitation signal $V_{exc}$ generates a response current $I_{res}$ in the capacitive sensor, which is converted back into a voltage signal by a current-to-voltage converter, preferably in the form of a transimpedance amplifier. This current-proportional voltage and the excitation signal $V_{exc}$ are measured by a high-performance oscilloscope and prepared for further digital analyses. An A/D converter with following programmable digital elements (FPGA) or an alternative circuit for data capture may be used instead of an oscilloscope for the same effect.

By using a multi-frequency excitation signal and following evaluation of the signal response by use of spectral analysis applying the fast Fourier transformation (FFT), the time to obtain a complete result can be dramatically reduced. A very preferred excitation signal is a multi-sine signal, combining the possibilities of a simultaneous capturing of all discrete frequency components with a satisfying signal quality for a real-time monitoring application. The signal is generated by adding up multiple sine waves, while each wave can be chosen with its particular frequency $f_n$, amplitude $a_n$ and phase $\varphi_n$ according to the following equation:

$$u(t) = \sum_{n=1}^{N} a_n \cos(2\pi f_n t + \varphi_n)$$

u(t): signal
fn: frequency
an: amplitude
t: time
φn: phase

Metrics are needed to evaluate the quality of the generated signals and the corresponding impedance spectra. To determine the signal quality in the time domain the crest-factor (CF) is used to determine how much signal amplitude is needed to introduce a certain amount of energy into a system. The quantity CF is the ratio between the peak value of a signal and the effective root-mean-square value of the signal. For a signal s(t) measured over a time interval the CF is calculated by:

$$CF(s) = \frac{\max_{t \in [0,T]} |s(t)|}{\sqrt{\frac{1}{T} \int_0^T |s(t)|^2 dt}}$$

CF(s): crest factor
s(t): signal
t: time

Complimentary to the crest-factor, the root mean square (RMS) voltage of the multi-sine for a limited voltage level is used as a metric for the energy density. For further insight, the signal-to-noise ratio (SNR) is applied. The SNR is the ratio between the power of signal and the power of present background noise.

The more frequencies which are incorporated in the multi-sine signal, the better the spectral resolution of the impedance spectrum. However, the amount of energy being introduced to the system for a single frequency component is inversely proportional to the number of excited frequencies N. It was found that for a satisfying frequency resolution at least 10 different frequencies are needed. For N>30, the single amplitudes, especially for the low frequencies, drop below a level where they cause a measurable effect in the specimen as the maximum value of the applied voltage signals was limited to 10 $V_{PP}$.

A number of 5 to 10 frequencies per decade has proven to be a good compromise between spectral resolution and sufficient energy input. The signal was additionally optimized in terms of amplitude, phase angle and frequency distribution.

The parameters indicate that the combination of a second order power function and phase offsets calculated according to Newman give the best result with the lowest CF and simultaneously the highest RMS voltage.

Figure 2:
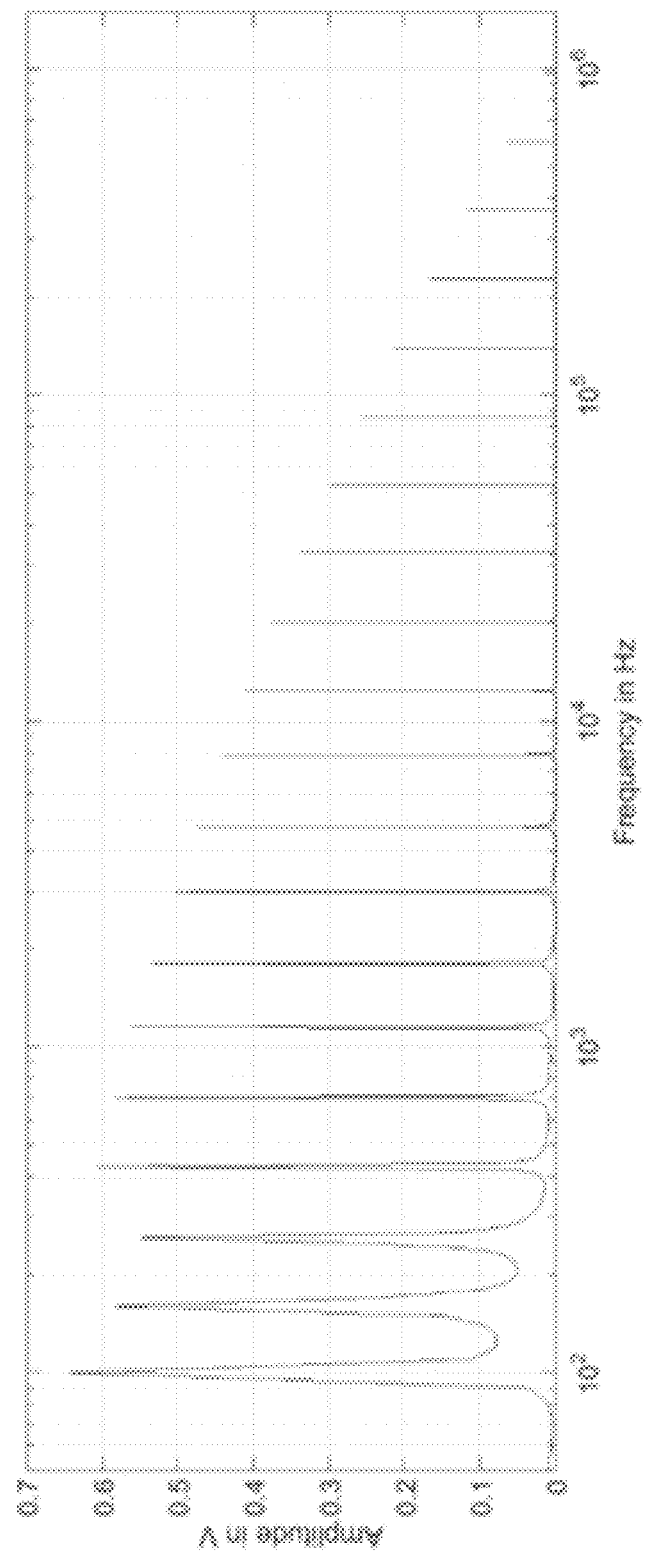
FIG. 2 shows a FFT spectrum of a preferred created excitation signal

FIG. 2 shows the corresponding FFT spectrum of a preferred created excitation signal. Due to the repeating nature of the signal higher frequency components appear more often than low frequency components. To keep the energy input for each frequency component at a similar level, the amplitudes decreases with rising excitation frequency.

In the course of data processing, the digitalized excitation and sensor or response signals are evaluated based on Fourier-based evaluation algorithms, wherein material-specific characteristic values are assigned to the spectrally present signal information contained in the response signals as part of the signal analysis, which may be displayed visually in the form of a graph, for example.

Figure 3:
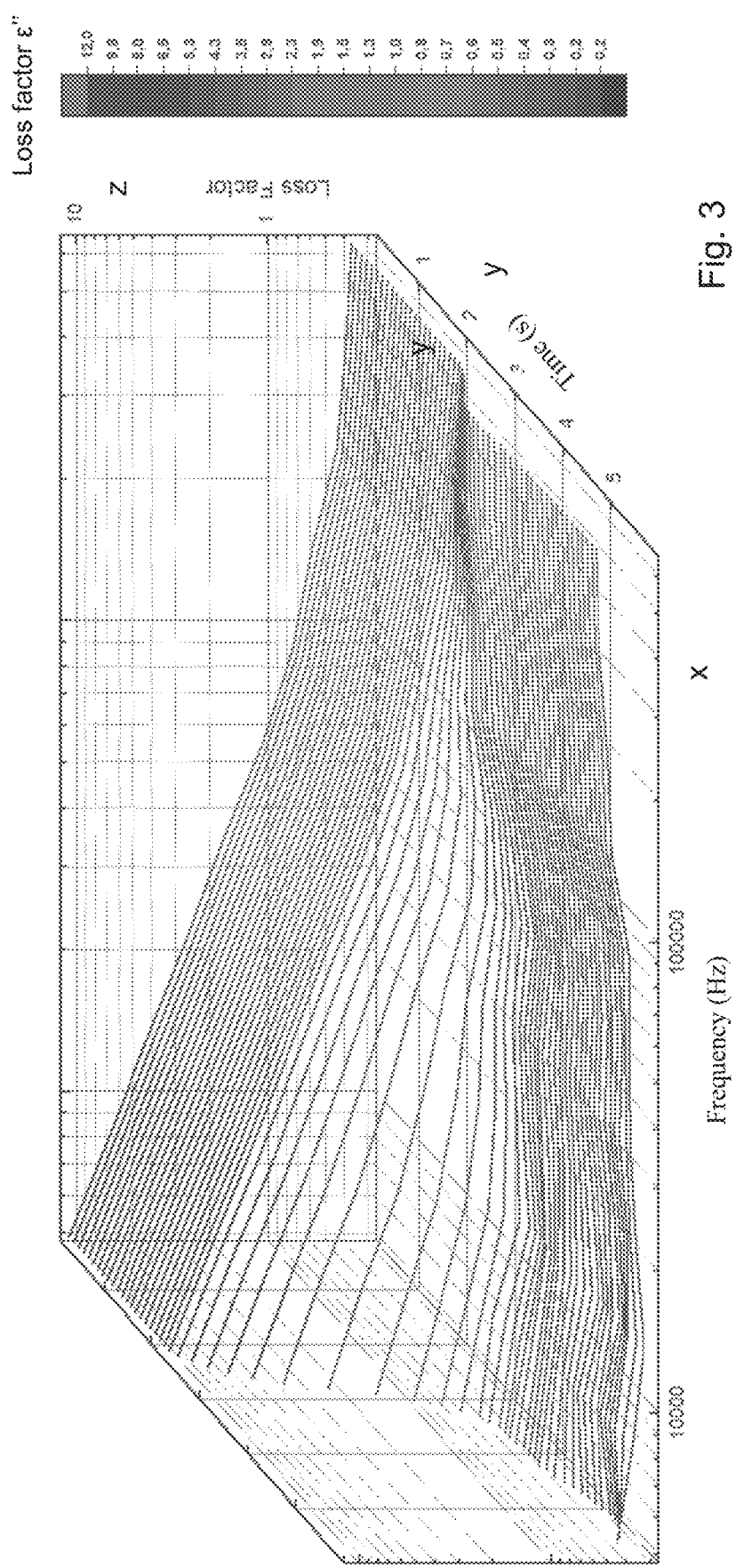
FIG. 3 shows a graphical representation of the measurement results relating to the loss factor ε" for a section of the frequency spectrum.

An example of such a display is shown in FIG. 3, which shows the progression of the loss factor ε" over the curing cycle of an industrial adhesive. In the graph shown, the x-axis corresponds to the frequency axis, the z-axis corresponds to the loss factor and the y-axis corresponds to the time axis. Each measurement line corresponds to a sensor signal which was recorded at a certain point in time z and each of which comprises a spectral functional progression which corresponds to the loss factor ε" as a function of the excitation frequency.

The measurement assembly according to the invention may be used for measuring dynamic impedances of any kind. The calculated characteristic values which are assignable to the respective material properties may be used to characterize and evaluate primarily curing processes. For materials and material combinations with known dielectric properties, the system may also be used for material characterization. In the case of an online evaluation of the data, the measurement assembly may be used with the data evaluation to monitor and control production processes, for example, curing processes of resins. Mixing ratios of various materials with known dielectric properties can also be determined. Aging processes of various materials may be monitored on the basis of time-induced changes in the material properties. The phase changes of thermoplastics are characterized by altered dielectric properties which can be detected with the described measurement system.

For example, the curing behaviour of adhesives that are activated by UV-light was investigated. The adhesive examined is a solvent-free single component adhesive based on a modified urethane acrylate. The measurements were conducted with flat, interdigital sensors, also called comb electrodes, which were cleaned with acetone to minimise distorting influences on the measurements. The material samples were irradiated and cured with a UV lamp. During the measurement, the measuring surface of the sensor used was entirely coated with the material for measurement to ensure that no other influences besides those of the sample were measured.

While the sample was irradiated and cured with a UV lamp, the rheological properties of the material were measured at a frequency of 1 Hz.

In order to obtain representative results, various material test methods were compared: Differential Scanning Calorimetry (DSC), rheology (mechanical test of viscoelastic properties) and the developed multi-frequency measurement system for dielectric analysis (DEA).

Figure 4:
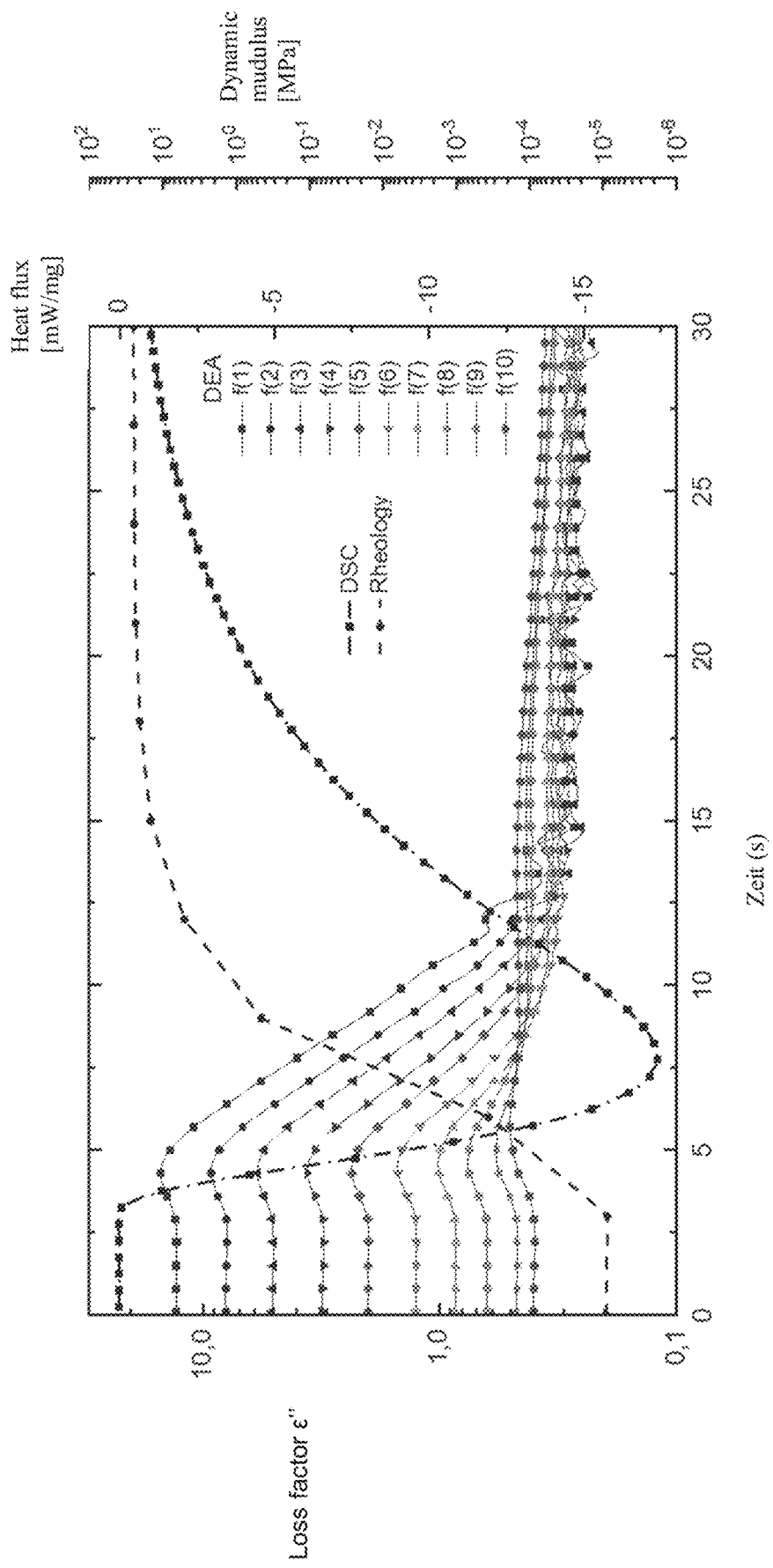
FIG. 4 shows a side-bis-side comparison of the measurements obtained with the measurement assembly according to the solution (DEA) and measurements using DSC and rheology.

The graph illustrated in FIG. 4 shows a side-by-side comparison of the measurements obtained with the measurement assembly according to the invention (DEA) and measurements using DSC and rheology.

To simplify the display, of the 20 simultaneously measured frequencies only 10 are plotted in a range of f(1)=5 kHz and f(10)=380 kHz. FIG. 4 shows the dielectric loss factor ε", which is a measure of the energy stored in the system. The measurement results of the heat flux and the dynamic modulus calculated from the rheology measurements are displayed for comparison purposes. It will be observed that the energy view of the curing cycle by the DSC measurement is not able to reflect the rapid curing process correctly. This process begins after about 3 s with the irradiation by UV light. This is followed by a short rise in the signal, which is attributable to relaxation processes in the material. After a global maximum is reached for the respective frequency, the signal drops to a minimum. Reaching this value coincides with the end of the curing cycle. The rheology measurements show a similar, though reciprocal progression of the measurements with the DEA system. In contrast to the other two systems, the DEA measuring system is capable of representing the brief relaxation process shortly after the UV irradiation is begun. The system delivers spectroscopic results for each measurement point without the need to carry out a time-consuming frequency sweep.

The device and method according to the invention have proven feasibility for the spectroscopic monitoring of reactive UV curing resins. Now the frequency dependent behaviour becomes accessible in real-time. Because 20 data points over the entire bandwidth of the system are captured time synchronously a curve for each time step can be created. The lowest frequency used to monitor the reaction limits the time resolution. Therefore, the proposed system and method overcome the limitations typically accompanied by standard DEA systems which are commercially available. The same is true for commercial vector network analyser or LCR-meters, which both use frequency sweeps for spectroscopic analysis.

The use of time synchronous data opens up new possibilities of reaction monitoring, for example to determine the conversion of reaction partners by the use of the frequency dependent permittivity.

The measurements shown here disclose the potential and unique selling point of the measuring system: which makes possible obtaining broadband results from impedance measurements for each time-discrete measurement point. The excitation signal which is used eliminates the need for a sequential consideration of the individual frequencies.

The invention claimed is:

1. An assembly for measuring electrical and dielectric properties of a material having dielectric properties which vary over time, comprising: a sensor that generates an electrical field interacting with the material and which is connected indirectly or directly to a signal generator that generates an excitation signal that is applied to the sensor which generates a sensor signal depending on the electrical and dielectric properties of the material; an analog-digital converter for converting the excitation signal and the sensor signal or analog signals derived therefrom into a digital excitation signal and digital sensor signal which is supplied to a processor-based evaluation unit; and wherein the signal generator generates a multifrequency signal of a predetermined bandwidth as the excitation signal; wherein the multifrequency signal comprises at least two simultaneous excitation modes with each mode having different excitation frequencies and different excitation signal amplitudes.

2. The assembly according to claim 1, wherein the multifrequency signal comprises excitation modes, which are distributed at least partially within the predetermined bandwidth by one of the following distribution patterns:
   an even distribution with equidistant frequency spacing between respective spectrally
   adjacent excitation modes,
   statistical distribution, and
   distribution based on an algebraic or transcendent function.

3. The assembly according to claim 1, wherein the multifrequency signal is a multi-sine signal, with excitation modes which are each sinusoidal.

4. The assembly according to claim 1, wherein the sensor signal depends on electrical and dielectric properties of the material which comprises spectrally spread and simultaneous response signal components resulting from each excitation mode of the multifrequency signal.

5. The assembly according to claim 1, wherein excitation signal amplitudes of the excitation modes within the multifrequency signals are predetermined according to one of the following distribution patterns: statistical distribution, distribution based on an algebraic or transcendent function, based on the electrical and dielectric properties of the material, and uniform distribution with equidistant frequency spacing between two respective spectrally adjacent excitation modes.

6. The assembly according to claim 1, wherein the sensor is connected to at least one of a transimpedance amplifier and a transimpedance amplifier circuit.

7. The assembly according to claim 6, wherein the transimpedance amplifier amplifies the sensor signal with an amplification factor from 10 to 120 dB to obtain an amplified voltage sensor signal.

8. The assembly according to claim 1, wherein a Fourier transformation-based algorithm is implemented in the processor-based evaluation unit and performs a Fourier transformation on the digital sensor signal and the digital excitation signal, and that the processor-based evaluation unit contains one algorithm for calculating a frequency-dependent impedance assigned to the material and a frequency-dependent phase angle ($\theta$) between the excitation and sensor signals based on the digital excitation and sensor signal.

9. The assembly according to claim 8, wherein at least one algorithm is implemented in the processor-based evaluation unit, which can calculate at least one of the following material properties of the material can be based on at least one of frequency-dependent impedance, frequency-dependent phase angle ($\theta$), ion conductivity, ion viscosity, relative permittivity, imaginary permittivity, absolute permittivity and loss factor.

10. A method for measuring electrical and dielectric properties of a material having dielectric properties which vary over time, comprising: generating an excitation signal to create an electrical field interacting with the material, generating a sensor signal dependent on the electrical and dielectric properties of the material while the electrical field interacts with the material, and performing an evaluation based on the excitation signal and the sensor signal for determining the electrical and dielectric properties of the material, and wherein the excitation signal is generated as a multi-frequency signal having a predetermined bandwidth; wherein the excitation signal comprises at least two simultaneous excitation modes with each mode having different excitation frequencies and different excitation signal amplitudes.

11. The method according to claim 10, wherein the excitation signal is applied to the sensor which generates the electrical field interacting with the material.

12. The method according to claim 10, wherein the multifrequency signal comprises excitation modes, each having a distribution specified at least partially within the predetermined bandwidth by one of the following distribution patterns:
   even distribution with equidistant frequency spacing between respective spectrally
   adjacent excitation modes,
   statistical distribution, and
   distribution based on an algebraic or transcendent function.

13. The method according to claim 10, wherein the multifrequency signal is a multi-sine signal, having the excitation modes which are each sinusoidal.

14. The method according to claim 10, wherein generation of the sensor signal is performed such that the sensor signal which depends on the electrical and dielectric properties of the material comprises spectrally spread and simultaneous response signal components resulting from each of the excitation modes of the multifrequency signal.

15. The method according to claim 10, wherein excitation signal amplitudes of excitation modes within the multifrequency signals are predetermined according to one of the following distribution patterns: statistical distribution, distribution on the basis of an algebraic or transcendent function based on the electrical and dielectric properties of the material, and uniform distribution with equidistant frequency spacing between two respective spectrally adjacent excitation modes.

16. The method according to claim 10, wherein the sensor signal and the excitation signal are each converted into digital signals which are evaluated based on a Fourier transform-based algorithm,
and
performing an evaluation based on at least one algorithm and the excitation and sensor signals for calculating a frequency-dependent impedance assignable to the material and for calculating a frequency-dependent phase angle between the excitation signal and sensor signal.

17. The method according to claim 16, comprising determining at least one material property of the material based on at least one of frequency-dependent impedance and frequency-dependent phase angle ($\theta$) and
Ion conductivity, ion viscosity, relative permittivity, imaginary permittivity, absolute permittivity, loss factor.

* * * * *